US010295475B2

(12) United States Patent
Ritchey et al.

(10) Patent No.: US 10,295,475 B2
(45) Date of Patent: May 21, 2019

(54) INSPECTION OF MACHINED HOLES (71) Applicant: Rolls-Royce Corporation, Indianapolis, IN (US)

(72) Inventors: Andrew James Ritchey, Lafayette, IN (US); Michael George Glavicic, Indianapolis, IN (US)

(73) Assignee: Rolls-Royce Corporation, Indianapolis, IN (US)

(*) Notice: Subject to any disclaimer, the term of this patent is extended or adjusted under 35 U.S.C. 154(b) by 636 days.

(21) Appl. No.: 14/843,193

(22) Filed: Sep. 2, 2015

(65) Prior Publication Data

US 2016/0069813 A1    Mar. 10, 2016

Related U.S. Application Data (60) Provisional application No. 62/046,536, filed on Sep. 5, 2014.

(51) Int. Cl.
*G01N 21/88* (2006.01)
*G01N 21/954* (2006.01)
*G01L 3/24* (2006.01)

(52) U.S. Cl.
CPC ....... *G01N 21/8806* (2013.01); *G01N 21/954* (2013.01); *G01N 2201/02* (2013.01); *G01N 2201/12* (2013.01)

(58) Field of Classification Search
None
See application file for complete search history.

(56) References Cited

U.S. PATENT DOCUMENTS

| 3,986,010 | A |   | 10/1976 | Lankford et al. |
|---|---|---|---|---|
| 4,211,129 | A |   | 7/1980 | Wittkopp et al. |
| 4,440,529 | A |   | 4/1984 | Henslee et al. |
| 4,471,444 | A |   | 9/1984 | Yee et al. |
| 4,509,126 | A | * | 4/1985 | Olig .................. G05B 19/4163 318/561 |
| 4,514,797 | A |   | 4/1985 | Begin |
| 4,579,487 | A |   | 4/1986 | Lehmkuhl |
| 4,583,295 | A |   | 4/1986 | Gresock et al. |
| 4,563,897 | A |   | 6/1986 | Moore |
| 4,709,198 | A |   | 11/1987 | Ogo et al. |
| 4,644,335 | A |   | 12/1987 | Wen |
| 4,713,770 | A |   | 12/1987 | Hayes et al. |
| 4,741,231 | A |   | 5/1988 | Patterson et al. |
| 4,802,095 | A |   | 1/1989 | Jeppsson |
| 4,805,351 | A |   | 2/1989 | Dobson et al. |
| 4,918,616 | A |   | 4/1990 | Yoshimura et al. |

(Continued)

OTHER PUBLICATIONS

BlueSwarf, "BlueSwarf DC Kit, Tooling Cloud and Dashboards," Retrieved on Aug. 13, 2015, from http://www.blueswarf.com, 1 pp.

(Continued)

*Primary Examiner* — Anand S Rao
*Assistant Examiner* — Tyler B Edwards
(74) *Attorney, Agent, or Firm* — Shumaker & Sieffert, P.A.

(57) ABSTRACT

A method includes obtaining an image of a feature machined in a component with an imaging device, determining, by a computing device, a quality of the feature in the component based on the image of the feature, and storing, by the computing device, an indication of the quality of the feature in combination with a unique identifier for the feature in a non-transitory computer-readable medium.

14 Claims, 7 Drawing Sheets

(56) References Cited

U.S. PATENT DOCUMENTS

| | | | |
|---|---|---|---|
| 4,992,712 A | 2/1991 | Fujimoto et al. | |
| 5,001,931 A | 3/1991 | Nishimoto et al. | |
| 5,054,087 A | 10/1991 | Carbon et al. | |
| 5,076,102 A | 12/1991 | Sato et al. | |
| 5,125,188 A | 6/1992 | Ogawa et al. | |
| 5,170,358 A | 12/1992 | Delio | |
| 5,349,337 A | 9/1994 | McCormick | |
| 5,432,422 A | 7/1995 | Nagano et al. | |
| 5,481,483 A | 1/1996 | Ebenstein | |
| 5,517,310 A | 5/1996 | Paquette | |
| 5,663,894 A | 9/1997 | Seth et al. | |
| 5,768,137 A * | 6/1998 | Polidoro | G05B 19/182 382/152 |
| 5,816,122 A | 10/1998 | Benning et al. | |
| 5,921,726 A | 7/1999 | Shiozaki et al. | |
| 6,085,121 A | 6/2000 | Stern | |
| 6,161,055 A | 12/2000 | Pryor | |
| 6,241,435 B1 | 6/2001 | Huang et al. | |
| 6,566,835 B1 | 5/2003 | Yoshida et al. | |
| 6,655,189 B1 | 12/2003 | Smith | |
| 6,697,759 B2 | 2/2004 | Saarinen et al. | |
| 6,873,722 B2 | 3/2005 | Hercke et al. | |
| 6,963,396 B2 | 11/2005 | Kimberlin | |
| 7,016,052 B2 | 3/2006 | Bloch et al. | |
| 7,206,657 B2 | 4/2007 | Esterling | |
| 7,289,873 B2 | 10/2007 | Redecker et al. | |
| 7,333,218 B2 | 2/2008 | Vaidyanathan | |
| 7,369,225 B2 | 5/2008 | Messerschmidt et al. | |
| 7,381,017 B2 | 6/2008 | Wang et al. | |
| 7,388,980 B2 | 6/2008 | Vaidyanathan | |
| 7,437,935 B2 | 10/2008 | Hanna et al. | |
| 7,536,237 B2 | 5/2009 | Esterling | |
| 7,540,697 B2 | 6/2009 | Wang et al. | |
| 7,574,035 B2 | 8/2009 | Koonankeil | |
| 7,602,486 B2 | 10/2009 | McDaniel et al. | |
| 7,602,963 B2 | 10/2009 | Nightingale et al. | |
| 7,619,646 B2 | 11/2009 | Freifeld et al. | |
| 7,706,912 B2 | 4/2010 | Grant et al. | |
| 7,710,287 B2 | 5/2010 | Lange et al. | |
| 7,903,245 B2 | 3/2011 | Miousset et al. | |
| 7,903,865 B2 | 3/2011 | Li et al. | |
| 7,933,679 B1 | 4/2011 | Kulkarni et al. | |
| 7,933,749 B2 | 4/2011 | Chang et al. | |
| 8,005,574 B2 | 8/2011 | Inagaki | |
| 8,014,903 B2 | 9/2011 | Inagaki | |
| 8,049,901 B2 | 11/2011 | Aoki et al. | |
| 8,060,835 B2 | 11/2011 | Newcomer et al. | |
| 8,205,530 B2 | 6/2012 | Subramanian | |
| 8,229,598 B2 | 7/2012 | Suzuki et al. | |
| 8,256,590 B2 | 9/2012 | Suzuki et al. | |
| 8,317,440 B2 | 11/2012 | Roders | |
| 8,351,679 B2 | 1/2013 | Fukami | |
| 8,374,717 B2 | 2/2013 | Suzuki et al. | |
| 8,414,264 B2 | 4/2013 | Bolms et al. | |
| 8,490,526 B2 | 7/2013 | Subramanian | |
| 2002/0002414 A1 * | 1/2002 | Hsiung | G05B 15/02 700/95 |
| 2002/0031250 A1 | 3/2002 | Saito et al. | |
| 2004/0068394 A1 | 4/2004 | Meekawa et al. | |
| 2005/0116673 A1 | 6/2005 | Carl et al. | |
| 2005/0210986 A1 | 9/2005 | Dondi | |
| 2006/0064197 A1 | 3/2006 | Shiga et al. | |
| 2008/0047333 A1 | 2/2008 | Turrini et al. | |
| 2008/0063483 A1 | 3/2008 | Kawai et al. | |
| 2010/0029179 A1 | 2/2010 | Cloutier et al. | |
| 2010/0034609 A1 | 2/2010 | Doppenberg | |
| 2010/0161107 A1 | 6/2010 | Kappmeyer et al. | |
| 2011/0081216 A1 | 4/2011 | Ogura et al. | |
| 2011/0177627 A1 * | 7/2011 | Huegli | H01L 31/1824 438/15 |
| 2011/0254496 A1 | 10/2011 | Barkman et al. | |
| 2012/0010744 A1 | 1/2012 | Yamashita et al. | |
| 2012/0065766 A1 | 3/2012 | Yoshino et al. | |
| 2012/0101624 A1 | 4/2012 | Ueno | |
| 2012/0109360 A1 | 5/2012 | Nishimura et al. | |
| 2012/0154570 A1 | 6/2012 | Bunker et al. | |
| 2012/0158170 A1 | 6/2012 | Bornemann et al. | |
| 2012/0224048 A1 | 9/2012 | Trzcinski | |
| 2012/0253708 A1 | 10/2012 | Tanaka | |
| 2013/0164092 A1 | 6/2013 | Kondo | |
| 2013/0173046 A1 | 7/2013 | Kawana et al. | |
| 2013/0208951 A1 | 8/2013 | Salem et al. | |
| 2013/0211574 A1 | 8/2013 | Wang et al. | |
| 2013/0248495 A1 | 9/2013 | Leao et al. | |
| 2013/0253670 A1 | 9/2013 | Chung et al. | |
| 2013/0261987 A1 | 10/2013 | Grant et al. | |
| 2013/0304248 A1 | 11/2013 | Lange et al. | |
| 2013/0345851 A1 | 12/2013 | Kataoka et al. | |
| 2014/0005831 A1 * | 1/2014 | Naderer | B25J 9/1633 700/258 |
| 2014/0075754 A1 | 3/2014 | Barron et al. | |
| 2014/0216170 A1 | 8/2014 | Ma et al. | |
| 2014/0260623 A1 | 9/2014 | Salem et al. | |
| 2015/0145193 A1 | 5/2015 | Ogawa et al. | |
| 2015/0328771 A1 | 11/2015 | Yuelai et al. | |
| 2016/0070253 A1 | 3/2016 | Dunkin et al. | |
| 2017/0089684 A1 | 3/2017 | Grupp et al. | |

OTHER PUBLICATIONS

"Bayesian network," Wikipedia, the free encyclopedia, retrieved from https://en.wikipedia.org/wiki/Bayesian_network, Aug. 18, 2015, 15 pp.

Harrison et al., "Inspection of White Layer in Hard Turned Components Using Electrochemical Methods," American Society of Mechanical Engineers, Journal of Manufacturing Science and Engineering, vol. 129, No. 2, Apr. 2007, 11 pp.

Kalidindi et al., "Microstructure Informatics Using Higher-Order Statistics and Efficient Data-Mining Protocols," Enabling ICME, The Member Journal of the Minerals, Metals & Materials Society, Retrieved from http://www.tms.org/pubs/journals/JOM/JOMhome.aspx, vol. 63, No. 4, Apr. 2011, 8 pp.

Materials Resources LLC, Home of Microstructure Informatics, retrieved from http://www.icmrl.net/ Aug. 18, 2015, 2 pp.

Smith, "Machining Dynamics, Using Science to Optimize High Performance Milling in Your Shop," Modern Machines Webinar, BlueSwarf, Jun. 19, 2014, Retrieved from http://www.mmsonline.com/webinars, 1 pp.

TMAC, "Save Time and Money with Reduced Cycle Time," MT Connect Protocol, Caron Engineering, Retrieved Jul. 22, 2015, from http://www.caroneng.com, 6 pp.

TMAC MP, "Tool Monitoring Adaptive Control for Multi-Process Machines," Caron Engineering, Retrieved Jul. 22, 2015 from http://www.caroneng.com, 2 pp.

TMAC SP, "Save Time & Money Reduce Cycle Time Analyze Cutting Problems," Caron Engineering, Retrieved from http://www.caroneng.com on Jul. 22, 2015, 2 pp.

"BlueSwarf How it Works," Retrieved from http://www.theinnovationmachine.com/The%20Learning%20Library/BlueSwarf%20How%20it%20Works.pdf on Sep. 1, 2015, 2 pp.

U.S. Appl. No. 62/145,915, filed Apr. 13, 2015 by Mike R. Dunkin.

U.S. Appl. No. 62/166,903, filed May 27, 2015 by Mike R. Dunkin.

Kim et al., "Tool life improvement by peck drilling and thrust force monitoring during deep-micro-hole drilling of steel," International Journal of Machine Tools and Manufacture, vol. 49, 2009, 10 pp.

Zelinski, "A Subscription to Spindle Speeds," Modern Machine Shop, Posted Oct. 18, 2006, 2 pp.

BlueSwarf, "Go Green with Blue," BlueSwarf LLC, retrieved from http://www.blueswarf.com retrieved on Aug. 31, 2015, 1 pp.

"What is Chatter," BlueSwarf LLC, retrieved from http://www.blueswarf.com on Aug. 31, 2015, 6 pp.

Harper, "Chatter Myths: Pieces of the Puzzle in Maximized Machining," MoldMaking Technology, Posted Sep. 1, 2004, 5 pp.

Zelinski, "Dial Down or Dial Up, " Blue Swarf Special Edition, Modern Machine Shop, Mar. 2009, 12 pp.

Zelinski, "Find the Right Speed for Chatter-Free Milling," Modern Machine Shop, Mar. 15, 2000, 2 pp.

Zelinski, "High Speed Machining's Origin Moment," Modern Machine Shop, Feb. 17, 2010, 2 pp.

(56) References Cited

OTHER PUBLICATIONS

MetalMax, "The Complete Package for Machine-Tool Dynamic Characterization," BlueSwarf LLC, retrieved from http://www.blueswarf.com on Aug. 31, 2015, 2 pp.

Zelinski, "No Need for Speed," Modern Machine Shop, Mar. 20, 2008, 5 pp.

Zelinski, "Ten Questions About Chatter," Modern Machine Shop, Sep. 9, 2005, 2 pp.

Zelinski, "The Overhang Effect," Modern Machine Shop, Jan. 1, 2003, 5 pp.

Haber et al., "An investigation of tool-wear monitoring in a high-speed machining process," Sensors and Actuators A, vol. 116, 2004, 7 pp.

Li et al., "Discrete wavelet transform for tool breakage monitoring," International Journal of Machine Tools & Manufacture, vol. 39, Feb. 1999, 10 pp.

Turk et al., "Eigenfaces for Recognition," Massachusetts Institute of Technology, Journal of Cognitive Neuroscience vol. 3 No. 1, 1991, 17 pp.

Jackson, "A User's Guide to Principal Components," Wiley-Interscience Publication, John Wiley & Sons, Inc, Jan. 1991, 18 pp.

U.S. Appl. No. 62/046,558, filed Sep. 2, 2014 by Mike R. Dunkin.

CRAC-Chatter Recognition and Control | AcronymAttic, What does CRAC stand for? Retrieved on Apr. 8, 2016 from http://www.acronymattic.com/Chatter-Recognition-and-Control-(CRAC).html, 3 pgs.

MLI Labs Inc., High Performance Machining Specialists, Harmonizer, Retrieved on Apr. 8, 2016 from http://www.mfg-abs.com/live/?page_id=103, 1 pg.

Dr. Johannes Heidenhain, "Technical Information, Dynamic Efficiency-Working Efficiently and with Process Reliability", Sep. 2013, 8 pgs.

TMAC-MP, Tool Monitoring Adaptive Control, Retrieved on Apr. 8, 2016 from https://www.caroneng.com/products/tmac-mp, 6 pgs.

U.S. Appl. No. 62/145,915, filed Apr. 10, 2015 by Mike R. Dunkin.

Grzesik et al., "Surface Integrity of Machined Surfaces," Surface Integrity in Machining, Chapter 5, Jan. 2010, pp. 143-179.

\* cited by examiner

INSPECTION OF MACHINED HOLES

This application claims the benefit of U.S. Provisional Application No. 62/046,536, filed Sep. 5, 2014, which is incorporated by reference in its entirety.

This invention was made with government support under Contract No. W31P4Q-08-D-0047 awarded by the United States Army. The Government has certain rights in the invention.

TECHNICAL FIELD

The invention relates to machining and evaluation of machined surfaces.

BACKGROUND

The quality of machined features within metal components may vary even when a series of components is manufactured using the same equipment according to the same design and specifications. For example, the finish quality of machined surfaces may vary. Machining may cause some features to have damage, such as white layer damage. White layer is a layer of untempered metal on the surface, which resists etching and appears white on a micrograph after etching a sample. Machined components may be manually inspected after machining for quality and damage such as while layer damage.

SUMMARY

This disclosure is directed to techniques for evaluating the quality of machined components. In some examples, the machine tooling force may be monitored during machining to evaluate the quality of a machined component. For example, a higher tooling force may indicate white layer damage. In the same or different examples, the quality of a machined component may be automatically evaluated by an imagining system. In some particular examples, machined features with a component may be designated for follow-up inspection based on tooling forces monitored during the machining of those features.

In one example, this disclosure is directed to a method comprising machining a component with a machine tool to form a feature in the component, monitoring, by a computing device, while machining the feature into the component with the machine tool, horsepower of the machine tool used to machine the component, determining, by the computing device, a quality of the feature in the component based on the monitored horsepower, and storing, by the computing device, an indication of the quality of the feature in combination with a unique identifier for the feature in a non-transitory computer-readable medium.

In another example, this disclosure is directed to a system comprising a machine tool, and a computing device. The computing device is configured to send control signals to the machine tool for causing the machine tool to machine a component to form a feature in the component, monitor, while the machine tool machines the feature into the component, horsepower of the machine tool used to machine the component, determine a quality of the feature in the component based on the monitored horsepower, and store an indication of the quality of the feature in combination with a unique identifier for the feature in a non-transitory computer-readable medium.

In a further example, this disclosure is directed to a non-transitory computer-readable data storage medium having instructions stored thereon that, when executed by one or more processors of a computing device, cause the computing device to send control signals to a machine tool for causing the machine tool to machine a component to form a feature in the component, monitor, while the machine tool machines the feature into the component, horsepower of the machine tool used to machine the component, determine a quality of the feature in the component based on the monitored horsepower, and store an indication of the quality of the feature in combination with a unique identifier for the feature in a non-transitory computer-readable medium.

In another example, this disclosure is directed to a method comprising obtaining an image of a feature machined in a component with an imaging device, determining, by a computing device, a quality of the feature in the component based on the image of the feature, and storing, by the computing device, an indication of the quality of the feature in combination with a unique identifier for the feature in a non-transitory computer-readable medium.

In a further example, this disclosure is directed to a system for evaluating a quality of a feature machined in a component, the system comprising an imaging device, and a computing device. The computing device is configured to send control signals for causing the imaging device to capture an image of a feature machined in a component, determine a quality of the feature in the component based on the image of the feature, and store an indication of the quality of the feature in combination with a unique identifier for the feature in a non-transitory computer-readable medium.

In another example, this disclosure is directed to a non-transitory computer-readable data storage medium having instructions stored thereon that, when executed by one or more processors of a computing device, cause the computing device to send control signals to an imaging device for causing imaging device to capture an image of a feature machined in a component, determine a quality of the feature in the component based on the image of the feature, and store an indication of the quality of the feature in combination with a unique identifier for the feature in a non-transitory computer-readable medium.

The details of one or more examples of this disclosure are set forth in the accompanying drawings and the description below. Other features, objects, and advantages of this disclosure will be apparent from the description and drawings, and from the claims.

BRIEF DESCRIPTION OF DRAWINGS

FIGS. 5A-7B illustrate monitored horsepower and cooling fluid flow rates during the machining of different holes in combination with the machined holes.

DETAILED DESCRIPTION

Figure 1:
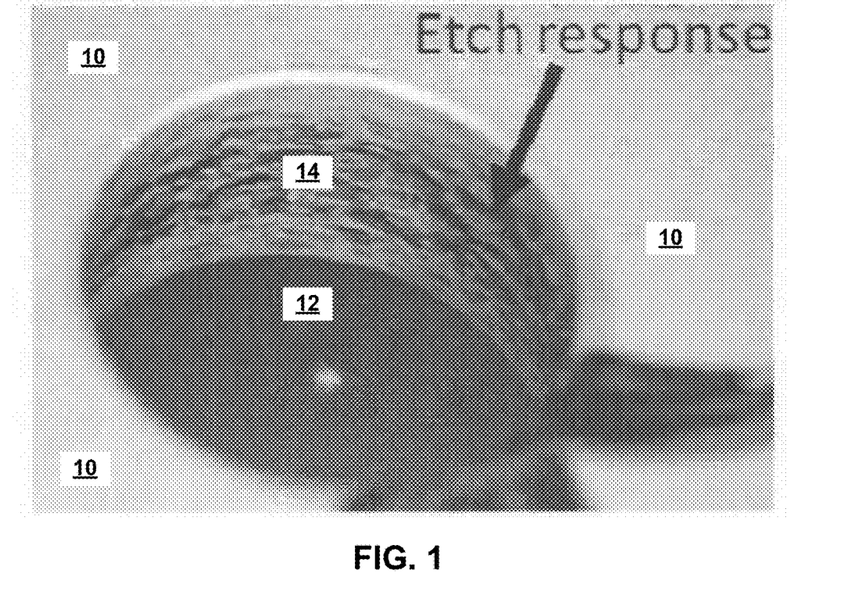
FIG. 1 illustrates a machined hole in a component, the machined hole exhibiting white layer damage.

FIG. 1 illustrates component 10 with machined hole 12. Surface 14 of machined hole 12 has been subjected to etching. As shown in FIG. 1, the etching has made white layer damage from the machining of machined hole 12 visible on surface 14.

Figure 2:
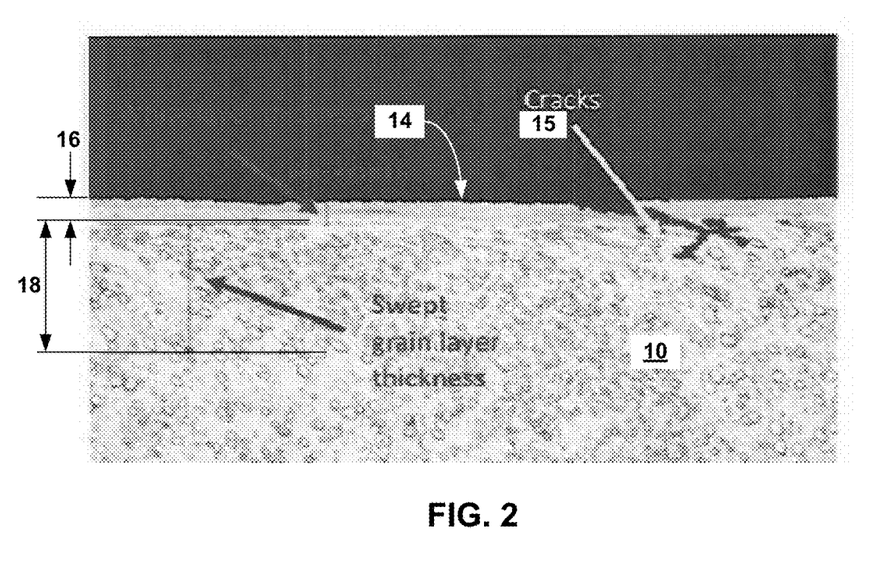
FIG. 2 is a close-up of a cross section of a machined surface of a component and illustrates a swept grain layer as well as a white layer from the machining of the component.

FIG. 2 is a close-up of a cross section of a machined surface 14 of component 10. Surface 14 was created from a machining operation, such as drilling, milling, turning or other machining operation. The machining operation created white layer 16 as well as swept grain layer 18. Surface 14, further includes cracks 15, which are also the result of the high stresses of the machining operation that created white layer 16. For example, white layer 16 is relatively brittle as compared to the rest of component 10, and cracks 15 may have propagated from smaller cracks in white layer 16.

During manufacturing, surface damage such as that illustrated in FIGS. 1 and 2 is generally undesirable. White layer damage is generally understood to be the result of an abusive interaction between a cutting element of a machine tool and the workpiece. Surface defects, such as white layer 16 and cracks 15 may be a major life determining factors for manufactured components because machining-induced surface damage has a very brittle nature and usually carries tensile residual stress. As demonstrated by FIG. 1, etching in an acidic bath followed by visual inspection of machined surfaces can be used to detect such surface defects. Following etching, machining defects present as lightly colored regions in contrast to the surrounding parent material.

Figure 3:
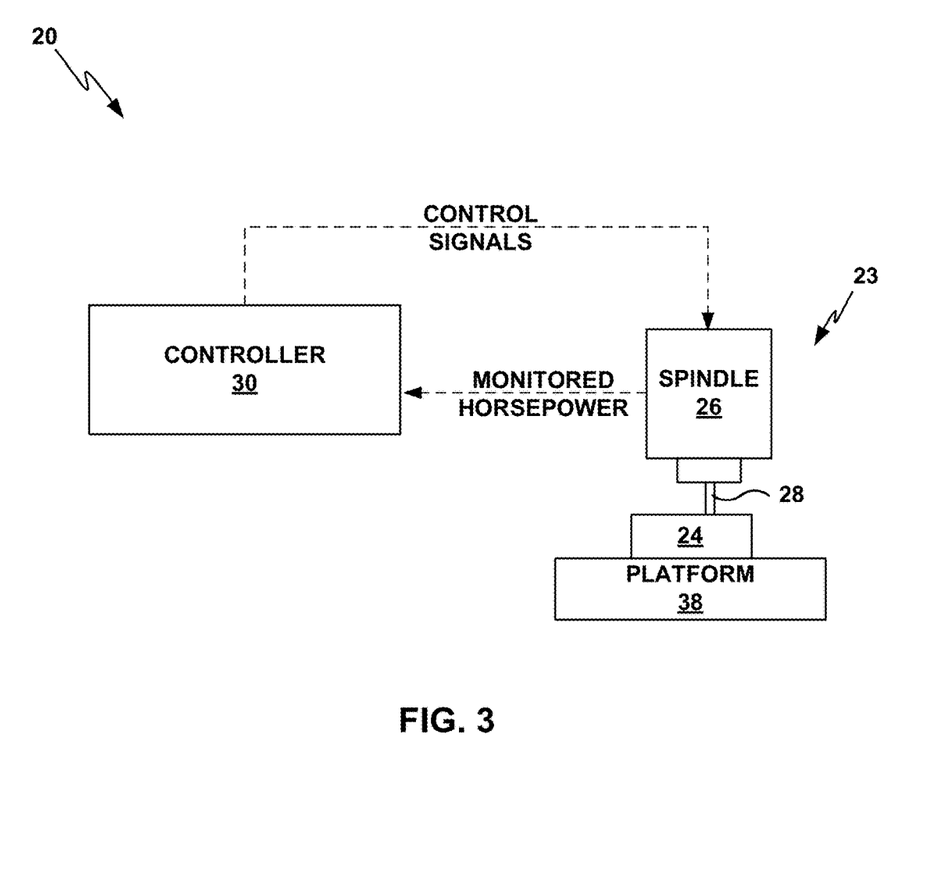
FIG. 3 illustrates a system including a machine tool and a computing device configured to determine a quality of a feature machined by the machine tool based on monitored horsepower of the machine tool.

As described herein, a surface quality of a machined feature may also be determined based on monitoring horsepower of a machine tool used to form the feature during the machining of the feature, for example, using a system such as system 20 of FIG. 3. System 20 includes machine tool 23 and controller 30, a computing device.

Machine tool 23 is configured to perform a machining operation on workpiece 24 with spindle 26 and cutting element 28. In one example, machine tool 23 may represent a computer numerical control (CNC) machine capable of performing routing, turning, drilling and/or other machining operations. Workpiece 24 is mounted to platform 38 in a manner that facilitates precise machining of workpiece 24 by machine tool 23. While the techniques disclosed herein may apply to workpieces of any materials, workpiece 24 may be metal subject to machining damage, including white layer damage.

Controller 30 represents a computing device configured to operate machine tool 23. In some examples, controller may be configured to adaptively machine workpiece 24 based on real-time or near real-time feedback of operational parameters associated with the operation of machine tool 23, such as one or more of horsepower of spindle 26, coolant pressure, coolant flowrate, cutting element vibration, and/or feed force of machine tool 23. Controller 30 may further be configured to determine a quality of a feature machined by machine tool 23 in workpiece 24 based on monitored horsepower of spindle 26 of machine tool 23.

In one particular example, controller 30 may operate to adjust the feed rate of spindle 26 and/or rotational speed of spindle 26 based on the monitored operational parameters in order to keep the monitored operational parameters within predefined limits. For example, controller 30 may operate to adjust the feed rate of spindle 26 and/or rotational speed of spindle 26 to prevent the monitored horsepower of spindle 26 from exceeding a predefined limit.

Machine tool 23 is configured to machine the component to form the feature in the component in response to the control signals sent from controller 30. In some examples, machine tool 23 may be configured to drill, mill or turn features into workpiece 24. For example, machine tool 23 may be configured to drill a through hole into workpiece 24 with spindle 26 or other rotary element.

In some particular examples, controller 30 may include multiple computing devices that combine to provide the functionality of controller 30 as described herein. For example, controller 30 may comprise a CNC controller that issues instructions to spindle 26 and positioning actuators of machine tool 23 as well as a separate computing device that monitors operational parameters of machine tool 23 and actively adjust the feed rate of spindle 26 and/or rotational speed of spindle 26 based on the monitored parameters. In some examples, such a computing device may represent a general purpose computer running software. Software suitable for actively controlling machining parameters includes Tool Monitor Adaptive Control (TMAC) software from Caron Engineering of Wells, Maine, United States.

Control signals from controller 30 for causing machine tool 23 to machine workpiece 24 may be based on a predetermined design of the feature and the monitored horsepower. In some examples, controller 30 evaluates monitored horsepower of spindle 26 against predetermined static thresholds. A computing device of controller 30 may then update the machining variables, such as the feed rate of spindle 26 and/or rotational speed of spindle 26, in real time and populates them to a CNC controller of controller 30 to adjust the feed rate of spindle 26 and/or rotational speed of spindle 26 in an effort to maintain spindle horsepower below a predetermined static thresholds or even maintain a relatively constant spindle horsepower.

In further examples, controller 30 may further monitor one or more of coolant pressure, coolant flowrate, cutting element vibration, and feed force of machine tool 23. In the same or different examples, controller 30 may apply preset processing thresholds for one or more of the monitored machining variables and maintain operations within the preset thresholds, for example, by varying a rotational velocity and/or linear velocity of cutting element 28 is real-time. Such preset processing thresholds may improve tooling life and provide reduce residual stresses due to machining operations.

In addition, by monitoring horsepower of spindle 26, and potentially other machining variables, such as one or more of coolant pressure, coolant flowrate, cutting element vibration, and feed force of machine tool 23, controller 30 further facilitates determining a quality of a feature machined by machine tool 23 in workpiece 24. For example, controller 30 may assess monitored horsepower of spindle 26 by evaluating overall maximum horsepower, variation between maximum and minimum horsepower, along with frequency of horsepower variation. In this manner, controller 30 may operate to identify machined features that are likely to have white layer damage or other quality issues automatically based on monitored horsepower of spindle 26, and potentially other machining variables, during the machining of such features.

Figure 4:
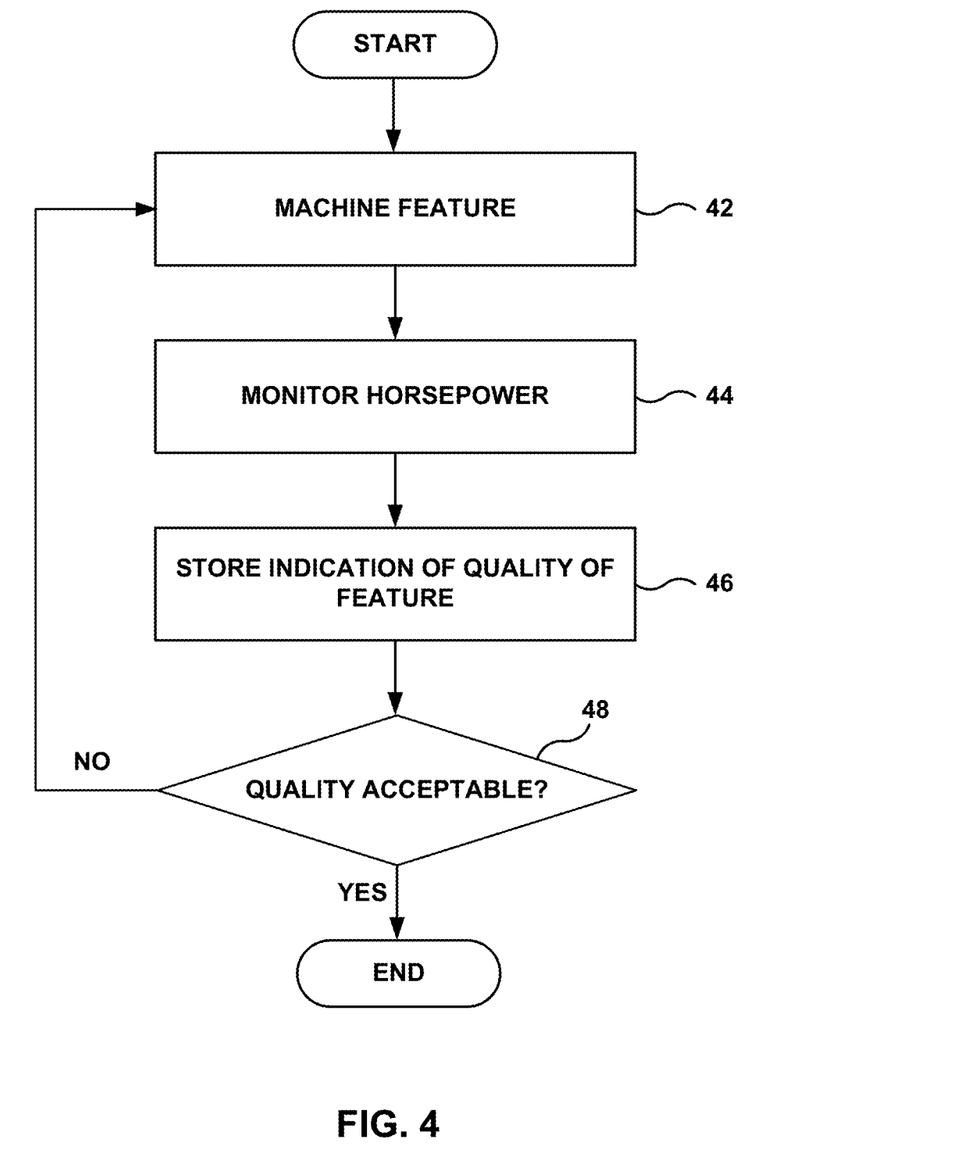
FIG. 4 is a flowchart illustrating example techniques for determining a quality of a machined feature in a component based on monitored horsepower.

As discussed in further detail with respect to FIG. 4, controller 30 may flag features in which a determined quality is outside of specifications for further evaluation and/or a secondary rework operation to improve a surface quality of the machined feature. In some examples, a machined feature may be automatically subjected to a secondary rework operation before workpiece 24 is removed from platform 38.

In this manner, system 20 facilitates pre-inspection and a secondary rework operation of a feature prior to removal of workpiece 24 from platform 38. This may speed the manufacture of a component from workpiece 24 as compared to techniques in which workpiece 24 is only inspected after removal from platform 38. In addition, the ability of pre-inspecting features may result in improved surface quality of machined features within workpiece 24 such that fewer defects may be found during a subsequent visual inspection. In addition, system 20 provides improved confidence in the integrity of a machined component as a surface quality of the machined feature may be determined based on both monitored horsepower of spindle 26 as well as a later visual inspection.

FIG. 4 is a flowchart illustrating example techniques for determining a quality of a machined feature in a component based on monitored horsepower. For clarity, the techniques of FIG. 4 are described with respect to system 20 of FIG. 3.

Workpiece 24 is mounted to platform 38, and controller 30 initiates a machining operation with machine tool 23 on workpiece 24 to form a feature in workpiece 24 (42). During the machining of the feature into workpiece 24, controller 30 monitors horsepower of machine tool 23, such as the horsepower of spindle 26 (44).

Then, controller 30 determines a quality of the machined feature in workpiece 24 based on the monitored horsepower (48). For example, controller 30 may determine a quality of the machined feature in workpiece 24 based on maximum horsepower, variation between maximum and minimum horsepower, along with frequency of horsepower variation of spindle 26. Example horsepower signals indicative of white layer damage are illustrated in FIGS. 5A-7B. If the quality of the machined feature in workpiece 24 is not acceptable, controller 30 may automatically reworking the feature with machine tool 23 based on the determination of the quality of the feature by returning to step 44. Alternatively, or in addition to automatically reworking the feature with machine tool 23, controller 30 may automatically store an indication that the machined feature in workpiece 24 is outside a predetermined tolerance range. The indication of the quality of the feature may include an indication the feature may include white layer damage.

Controller 30 also stores an indication of the quality of the feature in combination with a unique identifier for the feature in a non-transitory computer-readable medium (46). Controller 30 may also present the indication of the quality of the feature to a human operator via a user interface of controller 30 or via a network connection to a remote computing device.

In some examples, as part of machining the feature in workpiece 24, controller 30 may send control signals to machine tool 23, the control signals being based on a predetermined design of the feature and the monitored horsepower. For example, controller 30 may operate to adjust the feed rate of spindle 26 and/or rotational speed of spindle 26 based on the monitored operational parameters in order to keep the monitored operational parameters within predefined limits. For example, controller 30 may operate to adjust the feed rate of spindle 26 and/or rotational speed of spindle 26 to prevent the monitored horsepower of spindle 26 from exceeding a predefined limit.

Experimental Results

Figure 5A:
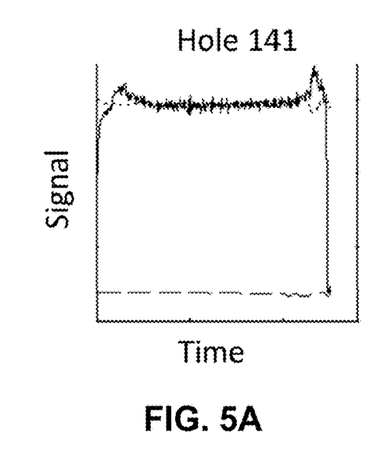
Figure 5B:
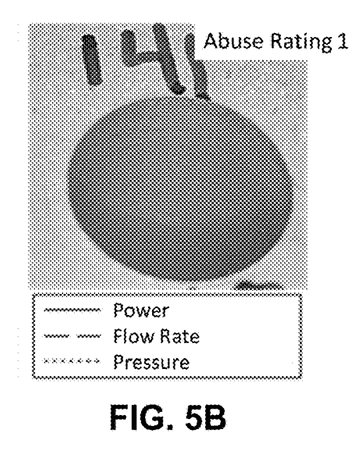

FIGS. 5A-7B illustrate monitored horsepower and cooling fluid flow rates during the machining of different holes in combination with the machined holes. In particular, FIG. 5A illustrates the horsepower and cooling fluid flow rates for machined hole 141, which is illustrated in FIG. 5B. Machined hole 141 presents an acceptable surface free of white layer damage and other defects.

Figure 6A:
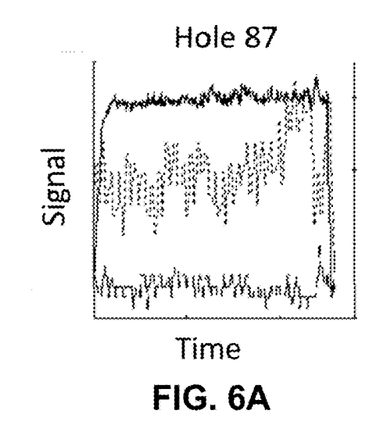
Figure 6B:
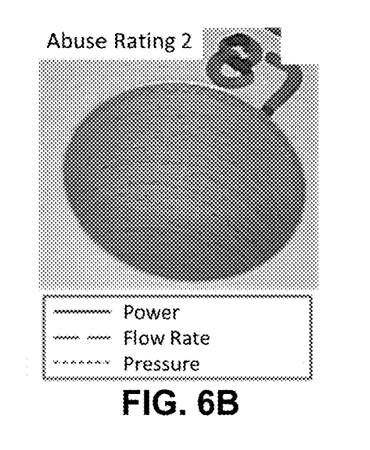

In contrast, FIG. 6A illustrates the horsepower and cooling fluid flow rates for machined hole 87, which is illustrated in FIG. 6B. Machined hole 87 presents a surface of moderate white layer damage. Machined hole 87 may be slated for rework in order to improve the surface quality of machined hole 87.

Figure 7A:
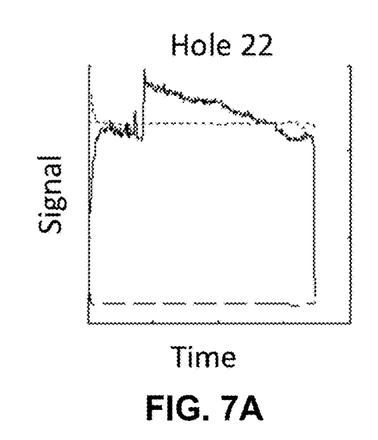
Figure 7B:
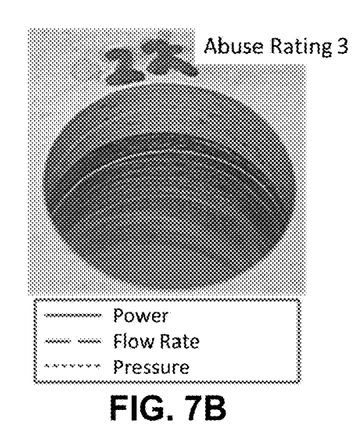

Likewise, FIG. 7A illustrates the horsepower and cooling fluid flow rates for machined hole 22, which is illustrated in FIG. 7B. Machined hole 22 presents a surface of excessive levels of white layer damage. Machined hole 22 may be slated for rework in order to improve the surface quality of machined hole 22, or potentially require scrapping the component including machined hole 22 if machined hole cannot be reworked to provide an acceptable surface within specified dimensional tolerance limits.

Comparison of the curves of FIGS. 5A, 6A and 7A illustrates the repeatable correlation between white layer damage and spindle horsepower and cooling fluid flow rates. While each of holes 141, 87 and 22 were machined according to the same specifications, using the same system, tooling and feedrates, as shown best in FIG. 7A, the maximum horsepower of the spindle varies according to the white layer damage in that higher horsepower of the spindle corresponds to increase severity of white layer damage. Likewise, as shown best in FIG. 6A, increased variability of horsepower also indicates white layer damage. Similarly, as shown in FIG. 6A, highly variable cooling flow rates and pressures represent a separate indications of white layer damage.

Figure 8:
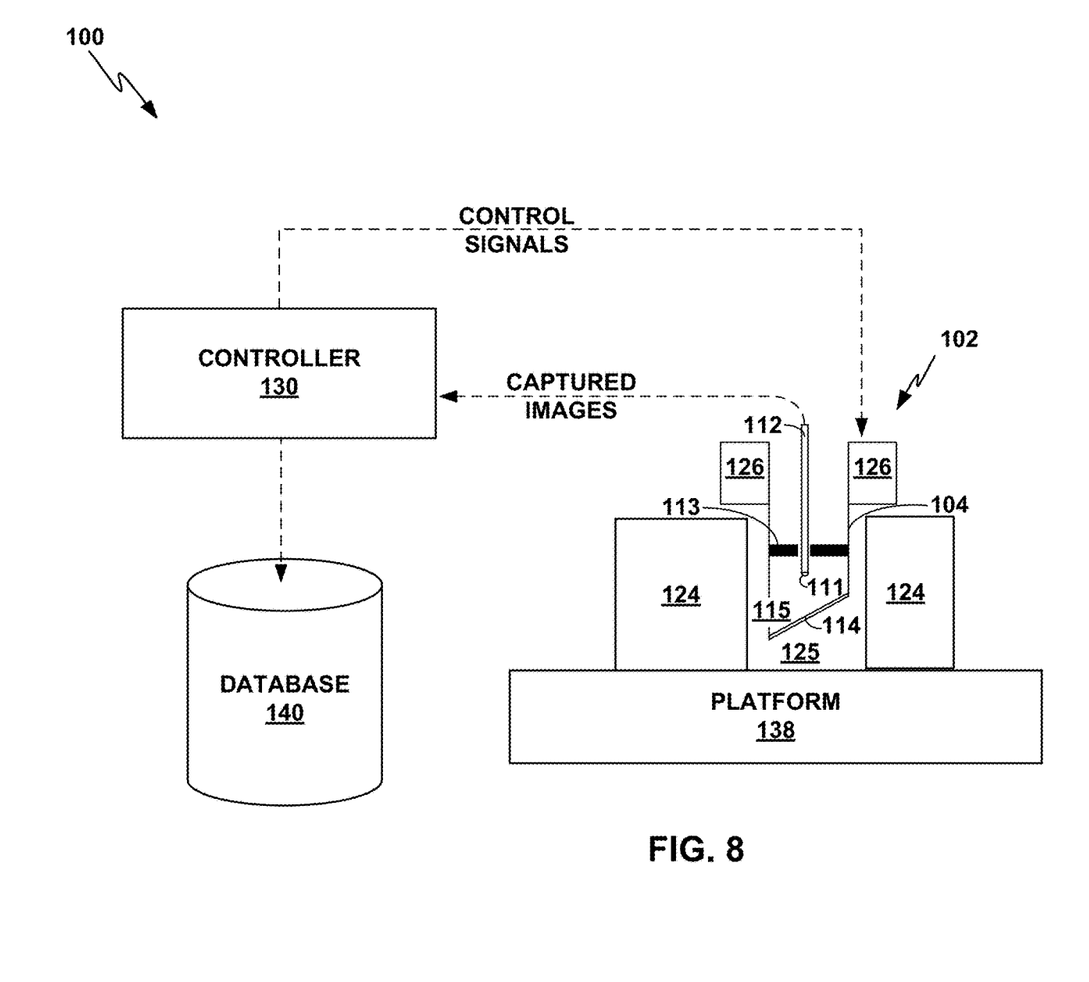
FIG. 8 illustrates a system including an imagining device and a computing device configured to determine a quality of a machined feature in a component based on an image of the component.

FIG. 8 illustrates system 100. System 100 includes an imaging device 102, controller 130 and database 140. Imaging device 102 includes camera 112, which may be a fiber optic camera. Camera 112 is mounted within tool sleeve 104 and supported by support structure 114 within tool sleeve 104. Mirror 114 is located at the bottom of tool sleeve 104 and functions to reflect light that passes through aperture 115 onto the lens and/or image sensor 111 of camera 112. Tool sleeve 104 including camera 112 is mounted within chuck 126. Chuck 126 which allows computer controlled positioning and rotation of camera 112 to facilitate capturing images of machined features in a component, and may be substantially similar to a CNC chuck.

As shown in FIG. 8, component 124 is mounted to platform 138 to facilitate capturing images of machined surfaces of component 124 with imaging device 102. In particular, imaging device 102 is located within through-hole 125 within component 124 in order to capture images of the machined surfaces of through-hole 125. In some examples, platform 138 may be the same as platform 38 such that images of machined surfaces of a workpiece or component may be captured at a common workstation immediately after machining the workpiece or component.

In other examples, a machined component may be positioned on platform 138 after a machining operation for inspection.

Controller 130 represents a computing device configured to operate imaging device 102. Imaging device 102 is configured to capture images of component 124 in response to the control signals sent from controller 130. In some particular examples, controller 130 may include multiple computing devices that combine to provide the functionality of controller 130 as described herein. For example, controller 130 may comprise a CNC controller that issues instructions to chuck 126 and positioning actuators of chuck 126 as well as a separate computing device that controls camera 112 and determines a quality of a machined feature in a component based on an image of the component. In some examples, such a computing device may represent a general purpose computer running software. In the same or different examples, all or a portion of controller 130 may be part of controller 30.

Controller 130 determines a quality of a machined feature in component 124 based on images of machined surfaces of component 124. In some examples, machined features of component 124 may be subjected to an etchant prior to imaging with camera 112. The etchant will produce a dark coloring if swept grains and/or white layer has been produced to better facilitate the imaging analysis. For example, controller 130 may compare images of machined surfaces of component 124 to a database of previous images and based on a "best fit" a quantitative measure of etch response is assigned. In some examples, in-situ drilling conditions, such has horsepower or coolant pressure, as described above with respect to FIGS. 3-7 may be used as supplemental information to aid in the assessment of the quality of the surface of component 124. In additions, controller 130 may also use the images and in-situ drilling conditions to evaluate tool wear, such as evaluate the remaining number of holes that can be drilled with the specific bit before the risk of white layer damage becomes unacceptable.

While controller 130 may implement one or more of a variety of techniques to determine a quality of a machined feature in component 124, in some examples, controller 130 may implement one or more machine learning algorithms, such as Principle Component Analysis (PCA), Bayesian Belief Networks (BBN), k-Nearest Neighbor Learners (kNN) and/or Majority Learners (ML). Controller 130 may determine the quality of a hole, such as hole 125 based on training data that is provided both prior to the inspection of hole 125 and other machined components as well as additional data added during the manufacturing of a series of components. Visual inspection by a technician and microscopic material reports may be used to provide baseline information to the machine learning algorithms.

Controller 130 may be connected to database 140, which includes a non-transitory computer-readable medium storing inspection information and/or the machine learning algorithms necessary to accurately assess the quality of hole 125 being inspected. In addition, controller may update database 140 with information derived during the inspection of hole 125, such as an indication of the quality of the feature in combination with a unique identifier for the feature.

Figure 9A:
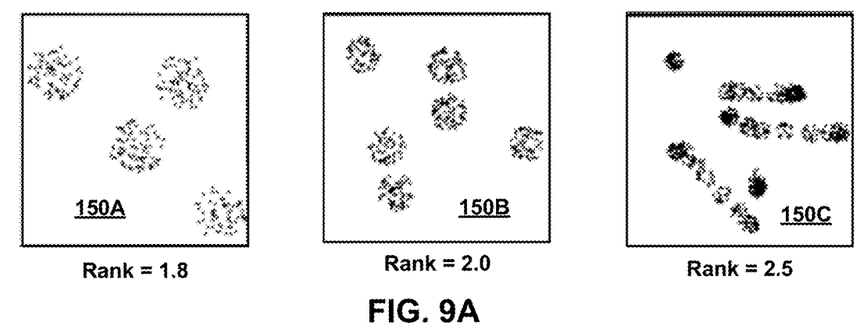
FIGS. 9A and 9B illustrate an example series of images that facilitate Principal Component Analysis of an image of a machined feature in a component to determine a quality of a machined feature based on the image.
Figure 9B:
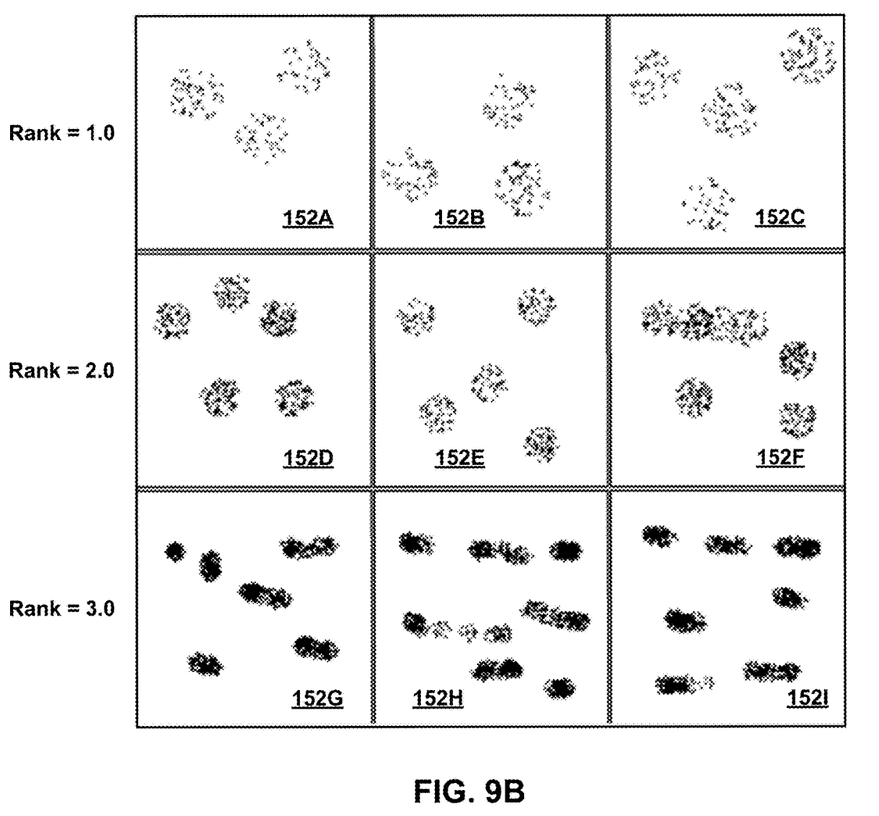

FIGS. 9A and 9B illustrate an example series of images that facilitate PCA of an image of a machined feature in a component to determine a quality of a machined feature based on the image. The image within a database that is the most similar to an input is automatically retrieved by a PCA search algorithm along with any other specific data associated with that particular image. Thus, PCA may be used to evaluate a captured image of a machined feature, such as a drilled hole.

Input images 150A-150C are illustrated in both FIG. 9A, whereas database images 152A-152I are illustrated in FIG. 9B. Database images 152A-152I are sorted into three rows. Database images 152A-152C in the first row represent a ranking of 1.0 for the purposes of this example. Similarly, database images 152D-152F in the second row represent a ranking of 2.0, and database images 152G-152I in the third row represent a ranking of 3.0.

In one simple example of PCA, as represented by FIG. 9A, input image 150A is first compared to each of database images 152A-152I using PCA to find the ranking of input image 150A as relative to the defined rankings of the database images. In this instance, based on relative similarities of input image 150A to database images 152A-152I using PCA, input image 150A is assigned a ranking of 1.8. Using the same techniques, input image 150B is compared to each of database images 152A-152I using PCA and assigned a ranking of 2.0, and input image 150C is compared to each of database images 152A-152I using PCA and assigned a ranking of 2.5.

Figure 10:
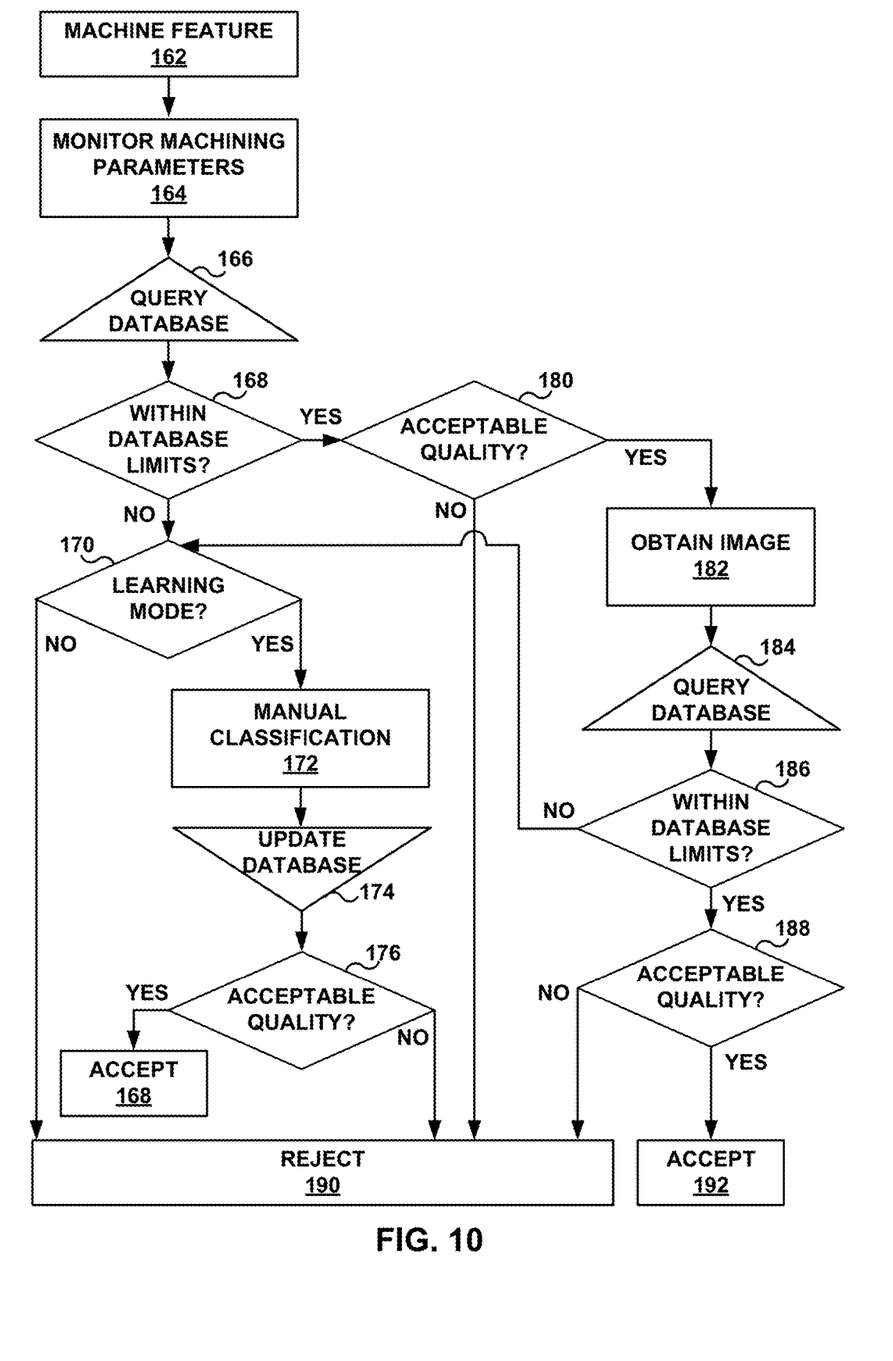
FIG. 10 is a flowchart illustrating example techniques for determining a quality of the machined feature in a component based monitored machining parameters and an image of the component.

FIG. 10 is a flowchart illustrating example techniques for determining a quality of the machined feature in a component based monitored machining parameters and an image of the component. For clarity, the techniques of FIG. 4 are described with respect to system 20 of FIG. 3 and system 100 of FIG. 8.

Workpiece 24 is mounted to platform 38, and controller 30 initiates a machining operation with machine tool 23 on workpiece 24 to form a feature in workpiece 24 (162). During the machining of the feature into workpiece 24, controller 30 monitors machining parameters, of machine tool 23, such as the horsepower of spindle 26, vibrations and/or cooling fluid flow, (164). Then, controller 30 queries database 140 to compare the monitored parameters with the parameters within database 140 (166). Controller 30 determines whether the monitored parameters are within the range limits of parameters within database 140 (168).

If the monitored parameters are not within the range limits of parameters within database 140, and controller 30 is not in a learning mode (170), the machined feature is rejected (190). Following rejection, the machined feature may be reworked as described with respect to FIG. 4. If the monitored parameters are not within the range limits of parameters within database 140, during a learning mode (170), database 140 may be updated with the monitored parameters (174) following a manual classification of the machined features in workpiece 24 (172). For example, the manual classification of the machined features may include a visual inspection of the machined features. Updating database 140 may include updating the database to correlate the monitored parameters with the results of the manual classification. If, based on the manual inspection, the quality is acceptable, the machined feature may be accepted (168). If, based on the manual inspection, the quality is not acceptable, the machined feature may be rejected (190). Again, following rejection, the machined feature may be reworked as described with respect to FIG. 4.

If controller 30 determines that the monitored parameters are within the range limits of parameters within database 140 (168), controller 30 determines a quality of the machined feature in workpiece 24 based on the monitored machining parameters, such as horsepower (180). For example, controller 30 may determine a quality of the machined feature in workpiece 24 based on maximum horsepower, variation between maximum and minimum horsepower, along with frequency of horsepower variation of spindle 26. If the quality of the machined feature in workpiece 24 is acceptable, controller 30 may store an indication of the quality of the feature in combination with a unique identifier for the feature in a non-transitory computer-readable medium, such as database 140.

If the quality of the machined feature in workpiece 24 is not acceptable, controller 30 may automatically reworking the feature with machine tool 23 based on the determination of the quality of the feature. Alternatively, or in addition to automatically reworking the feature with machine tool 23, controller 30 may automatically store an indication that the machined feature in workpiece 24 is outside a predetermined tolerance range. Based on this indication, workpiece 24 may be indicated for further inspection, e.g., by system 100. Following the machining of workpiece 24, workpiece 24 may take the form of component 124.

Component 124 is positioned on platform 138 of system 100. In other examples, platform 138 may be the same as platform 38, such that component 124 does not have to be repositioned after machining prior to an imaging inspection. Controller 130 may obtain an image of a feature, such as hole 125 machined in a component 124, for example, by capturing an image with imaging device 102 (182). In some examples, all or a portion of controller 130 may be the same as controller 30. In some examples, machined surfaces of component 124 slated for inspection may be subjected to an etchant prior to imaging with camera 112 of imaging device 102. Then, controller 130 queries database 140 to compare the captured image with captured images within database 140 (184). Controller 130 determines whether the image of the feature is within the limits of database 140 such that a quality of the machined feature may be evaluated, for example, using PCA, as described with respect to FIG. 9 (186).

If the image of the feature is within the limits of database 140, and controller 30 is not in a learning mode (170), the machined feature is rejected (190). Following rejection, the machined feature may be reworked as described with respect to FIG. 4. If the image of the feature is within the limits of database 140, during a learning mode (170), database 140 may be updated with the captured image (174) following a manual classification of the machined features in workpiece 24 (172). For example, the manual classification of the machined features may include a visual inspection of the machined features. Updating database 140 may include updating the database to correlate the captured image with the results of the manual classification. If, based on the manual inspection, the quality is acceptable, the machined feature may be accepted (168). If, based on the manual inspection, the quality is not acceptable, the machined feature may be rejected (190). Again, following rejection, the machined feature may be reworked as described with respect to FIG. 4.

If controller 130 determines that the image of the feature is within the limits of database 140 (186), controller 130 determines a quality of a feature, such as hole 125, in component 124 based on the image of the feature (188). Based on this determination, the machined feature may either be accepted (192) or rejected (190). For example, controller 130 may determine a quality of a feature based on the image of the feature using PCA as described previously. Controller 130 may store an indication of the quality of the feature in combination with a unique identifier for the feature in a non-transitory computer-readable medium, such as database 140. Controller 130 may also present the indication of the quality of the feature to a human operator via a user interface of controller 130 or via a network connection to a remote computing device.

The techniques described in this disclosure may be implemented, at least in part, in hardware, software, firmware, or any combination thereof. For example, various aspects of the described techniques, including controller 30 and controller 130, may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the one or more processors. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media.

Various examples of this disclosure have been described. These and other examples are within the scope of the following claims.

What is claimed is:
1. A method comprising:
    monitoring, by a computing device, horsepower of a machine tool used to machine a component during machining of a feature in the component with the machine tool;
    determining a quality of the feature based on at least one of maximum horsepower, variation between maximum and minimum horsepower, or frequency of horsepower variation;

in response to determining that the quality of the feature is outside a predetermined tolerance range, selecting the feature for evaluation by an imaging device;
obtaining an image of the feature with an imaging device;
applying, by the computing device, principle component analysis (PCA) to the image of the feature;
ranking, by the computing device, the image of the feature relative to defined rankings of database images of similar features based on the PCA;
determining, by the computing device, whether the feature in the component includes white layer damage based on the ranking; and
presenting, by the computing device, via a user interface, an indication of whether the feature includes white layer damage in combination with a unique identifier for the feature.

2. The method of claim 1, wherein the feature includes a hole, and wherein obtaining the image of the feature machined in the component with the imaging device includes:
locating an image sensor of the imagining device within the hole with a computer controlled positioning system; and
rotating the image sensor of the imaging device within the hole while capturing the image.

3. The method of claim 1, wherein the feature is machined in a metal portion of the component.

4. The method of claim 1, further comprising machining the component with a machine tool to form the feature in the component.

5. The method of claim 1, further comprising subjecting the feature in the component to an etchant prior to obtaining the image.

6. A system for evaluating a quality of a feature machined in a component, the system comprising:
an imaging device; and
a computing device, wherein the computing device is configured to:
monitor horsepower of a machine tool used to machine the component during machining of the feature in the component with the machine tool;
determine a quality of the feature based on at least one of maximum horsepower, variation between maximum and minimum horsepower, or frequency of horsepower variation;
in response to determining that the quality of the feature is outside a predetermined tolerance range, select the feature for evaluation by the imaging device;
send control signals that cause the imaging device to capture an image of the feature;
apply principle component analysis (PCA) to the image of the feature;
rank the image of the feature relative to define rankings of database images of similar features based on the PCA;
determine whether the feature in the component includes white layer damage based on the ranking; and
present, via a user interface, an indication of whether the feature includes white layer damage in combination with a unique identifier for the feature.

7. The system of claim 6, further comprising a positioning system,
wherein the imaging device is mounted to the positioning system,
wherein the computing device is further configured to send control signals that cause the positioning system to locate the imagining device adjacent the feature.

8. The system of claim 6,
wherein the feature includes a hole,
wherein the system further comprises a positioning system, wherein the imaging device is mounted to the positioning system,
wherein the computing device is further configured to send control signals for causing the positioning system to:
locate an image sensor of the imagining device within the hole; and
rotate the image sensor of the imaging device within the hole while capturing the image.

9. The system of claim 6, wherein the computing device is further configured to present the indication of the quality of the feature to a human operator.

10. The system of claim 6, wherein the computing device is further configured to store an indication that the feature in the component is outside a predetermined tolerance range.

11. The system of claim 6, wherein the system further comprises a machine tool, wherein the computing device is further configured to send control signals that cause the machine tool to form the feature in the component.

12. A non-transitory computer-readable data storage medium having instructions stored thereon that, when executed by one or more processors of a computing device, cause the computing device to:
monitor horsepower of a machine tool used to machine a component during machining of the feature in the component with the machine tool;
determine a quality of the feature based on at least one of maximum horsepower, variation between maximum and minimum horsepower, or frequency of horsepower variation;
in response to determining that the quality of the feature is outside a predetermined tolerance range, select the feature for evaluation by the imaging device;
send control signals to an imaging device that cause the imaging device to capture an image of the feature;
apply principle component analysis (PCA) to the image of the feature;
rank the image of the feature relative to defined rankings of database images of similar features based on the PCA;
determining whether the feature in the component includes white layer damage based on the ranking; and
present, via a user interface, an indication of whether the feature includes white layer damage in combination with a unique identifier for the feature.

13. The computer-readable data storage medium of claim 12, wherein the instructions stored on the computer-readable data storage medium, when executed by one or more processors of a computing device, further cause the computing device to issue control signals to a positioning system to locate the imagining device adjacent the feature.

14. The computer-readable data storage medium of claim 12, wherein the instructions stored on the computer-readable data storage medium, when executed by one or more processors of a computing device, further cause the computing device to store an indication that the feature in the component is outside a predetermined tolerance range.

* * * * *